United States Patent
Kuroiwa et al.

(10) Patent No.: US 6,350,772 B1
(45) Date of Patent: Feb. 26, 2002

(54) TREATMENT OF AUTO-IMMUNE DISEASES BY PHOTOCHEMOTHERAPY

(75) Inventors: Yukari Kuroiwa; Minako Araake, both of Yokohama; Hiroshi Suwa; Katsuo Aizawa, both of Tokyo, all of (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 09/297,810
(22) PCT Filed: Oct. 17, 1997
(86) PCT No.: PCT/JP97/03769
§ 371 Date: Jun. 16, 1999
§ 102(e) Date: Jun. 16, 1999
(87) PCT Pub. No.: WO98/19677
PCT Pub. Date: May 14, 1998

(30) Foreign Application Priority Data

Nov. 6, 1996 (JP) .............................................. 8-293061
Jul. 30, 1997 (JP) .............................................. 9-204711

(51) Int. Cl.[7] .......................... A61K 31/40; A61K 31/70
(52) U.S. Cl. .......................... 514/410; 514/429; 514/23
(58) Field of Search ................................. 514/410, 429, 514/23

(56) References Cited

U.S. PATENT DOCUMENTS 5,028,594 A * 7/1991 Carson ......................... 514/23
5,430,051 A * 7/1995 Aizawa et al. .............. 514/410

OTHER PUBLICATIONS

The Merck Manual, Berkow et al EE, Pocket Books NY pp. 246–247.*

* cited by examiner

*Primary Examiner*—Russell Travers
(74) *Attorney, Agent, or Firm*—Abelman, Frayne & Schwab

(57) ABSTRACT

As a novel photochemotherapeutical method for the treatment or prevention of an auto-immune disease, there is provided a method for treating an auto-immune disease, which comprises administering to the patient mono-L-aspartyl chlorin e6 or mono-L-glutamyl chlorin e6 or a pharmacologically acceptable salt thereof, followed by subjecting the blood vessel blood of the patient containing the administered compound to exposure with an ultraviolet ray or a laser light, thereby to excite said compound photochemically. This method is effective to decrease the level of auto-antibody in the blood of the patient and is also of high safety.

4 Claims, 1 Drawing Sheet

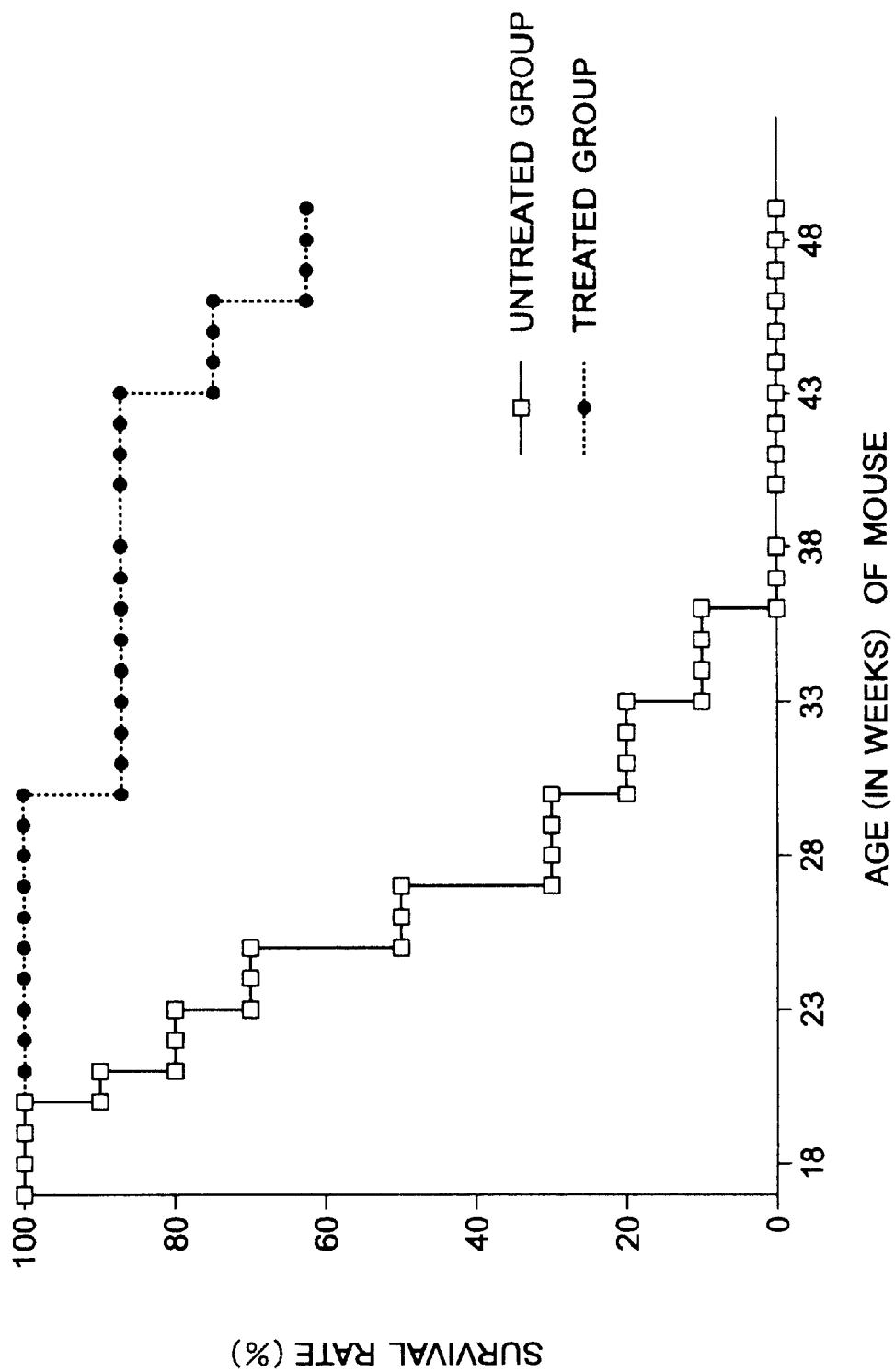

TREATMENT OF AUTO-IMMUNE DISEASES BY PHOTOCHEMOTHERAPY

This application is a 371 of PCT/JP97/03769 filed Oct. 17, 1997 which claims proof from Japanese Patent Application no. 9-204711 filed Jul. 30, 1997 and Japanese Patent Application no. 8-293061 filed Nov. 6, 1996.

TECHNICAL FIELD

This invention relates to a novel pharmaceutical composition for the therapeutic treatment of an auto-immune disease, which is to be used in a photochemotherapeutical method or a photodynamo-therapeutical method. This invention further relates to a novel photochemotherapeutical method for treating an auto-immune disease.

BACKGROUND ART

A photochemotherapeutical method or photodynamo-therapeutical method means a method of treating a disease by administration of such a photosensitive substance which is capable of displaying a therapeutic action for the first time i only when said substance is excited by being irradiated with an ultraviolet ray or a laser light. This method is a chemotherapy in which the therapy of a disease is effected by applying an irradiation of a light to a part or parts of the tissues of a living body of the patient where said photosensitive substance already administered is presented and accumulated, or by applying the light irradiation to a flow of intracorporeal blood containing said photosensitive substance or to a flow of blood as formed by extracorporeal circulation of the blood containing said photosensitive substance, so that said photosensitive substance is photochemically excited to display its therapeutic action.

A typical example of photosensitive substances, which were first proposed in the beginnings of the development of the photochemotherapy, is Photofrin. Photofrin has been used mainly for the purpose of the therapy of cancers because Photofrin has destructive actions against a variety of tumors. The function of Photofrin is explained to be such that Photofrin having n o activity by itself, but having an affinity for tumors is administered to a living body and thereby is allowed to accumulate itself around the newly formed vasculature of tumors, followed by irradiating the so accumulated Photofrin with a laser light of a certain wavelength range so that the energy of light is absorbed in said substance and the energy so elevated of said substance will excite the oxygen existing in the tumor cells to produce activated oxygen, and so that the activated oxygen gives obstructions to the tumor cells so as to cause necrosis of the tumor tissue.

Japanese Patent Publications Hei-6-88902 and Hei-6-89000 as well as United States Patent specification No. 4,675,338 disclose such fluorescent tetrapyrrole derivatives in which at least one carboxyl group of a certain tetrapyrrole compound having a plural number of side chains in the form of carboxyl groups or carboxylic acid types has been condensed via one or more amido-linkages with the amino group of an amino-dicarboxylic acid of 4 to 10 carbon atoms, for example, aspartic acid or glutamic acid, and which is, for example, mono-L-aspartyl chlorin e6 and mono-L-glutamyl chlorin e6, or salts thereof, along with processes for the preparation of said derivatives. Also disclosed therein are uses of these tetrapyrrole derivatives as a photochemotherapeutic agent for the purposes of diagnosis and therapy of tumors. The Japanese patent publications and U.S. patent specification referred to in the above further disclose that the above-mentioned fluorescent tetrapyrrole derivatives accumulated within the tumor tissue after their administration can be excited photochemically by subjecting to the irradiation with a strong light, for example, a laser beam and thereby can display an activity to kill the tumor cells.

With respect to the photochemotherapy, the prior art further reports, in addition to the above-mentioned therapy for cancers, that the use of mono-L-aspartyl chlorin e6 or mono-L-glutamyl chlorin e6, or their sodium salts is also applicable to the method for obstruction of newly formed blood vessels such as choroideae of eyes (refer to U.S. Pat. No. 5,633,275).

Further, U.S. Pat. No. 5,028,594 discloses the application of photochemotherapy to a method of the selective removal of hemopoietic cells participating in rheumatoid arthritis. On the other hand, Kenneth et al., propose a method for therapeutic treatment of proliferative arthropathia by application of photochemotherapy thereto, which method is characterized by the occurrence of destruction of synovial cells (see PCT Application International published specification WO94/17797).

As described above, there have been reported various applications of photochemotherapy for the destruction of tumor cells, removal of hemopoietic cells, destruction of proliferative synovial cells causative for articular rheumatism, and so on. Until now, however, there is no announcement as to such fact that the therapy of an autoimmune disease, for example, systemic lupus erythematosus, etc. was effected by applying photochemotherapy thereto.

An object of this invention is to provide a novel, pharmaceutical composition for the therapeutic treatment of a variety of auto-immune diseases, including systemic lupus erythematosus, systemic pachyderma, multiple myositis, dermatomyositis or polyarteritis nodosa and autoimmune hemolytic anemia and Hashimoto's thyroiditis, for example. Another object of this invention is to provide a novel photochemotherapeutical method for treatment of an auto-immune disease.

DISCLOSURE OF INVENTION

We, the inventors of this invention, have investigated on therapeutic agents for an auto-immune disease such as systemic lupus erythematosus, etc. to achieve the above-mentioned objects. And, we have now found that, when a photosensitive substance, mono-L-aspartyl chlorin e6 tetra-sodium salt (abbreviation: NPe6) which was described in Japanese Patent Publications Hei-6-88902 and Hei-6-89000 and U.S. Pat. No. 4,675,338 shown above and which has been examined in clinical testing for a photochemotherapy of malignant tumors is intravenously administered to mice employed as a model of a spontaneous systemic auto-immune disease, followed by irradiation of the mice with a laser light at 664 nm, either at such tissue of the whole parts or a part of the mice body, or at the circulating blood stream in the mice, which is or are containing said compound accumulated, the mono-L-aspartyl chlorin e6 tetra-sodium salt (i.e. NPe6) possesses an action capable of decreasing remarkably the antibody value of the auto-antibody in the blood of the mice. It is further expectable that as similar as NPe6, the free acid itself of mono-L-aspartyl chlorin e6 and mono-L-glutamyl chlorin e6 or tetra-sodium salt thereof, if excited photochemically, have the action capable of decreasing the antibody value of the auto-antibody in the blood, too. On the basis of these findings, we have completed this invention.

According to a first aspect of this invention, therefore, there is provided a pharmaceutical composition for photo-chemotherapeutically treating an auto-immune disease, characterized in that said composition contains as an active ingredient mono-L-aspartyl chlorin e6 or mono-L-glutamyl chlorin e6 or a pharmacologically acceptable salt thereof.

Mono-L-aspartyl chlorin e6 or mono-L-glutamyl chlorin e6 which is used as the active ingredient in the pharmaceutical composition for treatment of an auto-immune disease according to this invention, has been confirmed, by precise analyses of various NMR spectra, etc., to be such a tetrapyrrole derivative represented by the following formula (A)

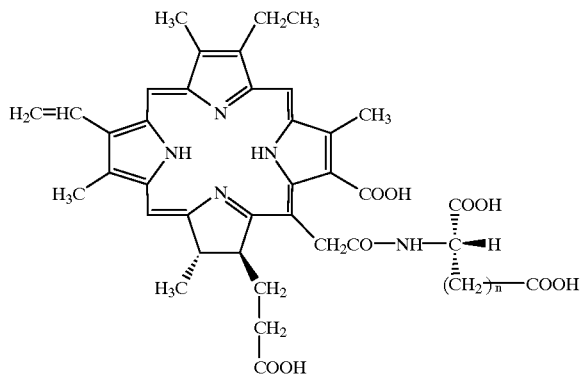

(A)

wherein n is 1 for mono-L-aspartyl chlorin e6, and n is 2 for mono-L-glutamyl chlorin e6.

Mono-L-aspartyl chlorin e6 mentioned above is such a compound of the formula(A) wherein the amino group of L-aspartic acid has been bonded, by an amido linkage, to one of the carboxyl groups as the side chains of the tetrapyrrole ring shown in the formula (A) above. Mono-L-aspartyl chlorin e6 may preferably be used in the form of tetrasodium salt thereof at the four carboxyl groups.

Mono-L-glutamyl chlorin e6 is such a compound of the formula (A) wherein L-glutamic acid has been bonded by an amido linkage in place of L-aspartic acid.

Mono-L-aspartyl chlorin e6 or mono-L-glutamyl chlorin e6 used as the photosensitive substance according to this invention may be in the form of a pharmacologically acceptable salt thereof and may generally be in the form of a salt which is formed by reacting with a pharmacologically acceptable base. As examples of such salts, there may be given those salts with sodium, potassium, calcium, magnesium, ammonium, triethylammonium, trimethylammonium, morpholine and piperidine.

Further, according to a second aspect of this invention, there is provided a method for photochemotherapeutically treating an auto-immune disease, which comprises administering orally or parenterally to a patient having an auto-immune disease to be treated a therapeutically effective amount of mono-L-aspartyl chlorin e6 or mono-L-glutamyl chlorin e6 or a pharmacologically acceptable salt thereof, irradiating the blood stream present in the blood vessel and containing the administered compound with an ultraviolet ray or a laser light, thereby to subject the mono-L-aspartyl chlorin e6 or mono-L-glutamyl chlorin e6 or salt thereof contained in said blood stream to exposure with the irradiating ultraviolet ray or laser light and to excite said compound photochemically, and effecting the administration of the mono-L-aspartyl chlorin e6 or mono-L-glutamyl chlorin e6 or salt thereof only once or two times or more and also repeating once more, twice or more times more the irradiation of the ultraviolet ray or laser light for the photochemical excitation of said compound contained in the blood stream, until the antibody value of the auto-antibody which is present in the blood of the patient and is specific to the auto-immune disease to be treated has been decreased significantly.

In the therapeutic method according to the second aspect of this invention, mono-L-aspartyl chlorin e6 or mono-L-glutamyl chlorin e6 or a salt thereof, when administered parenterally, may be administered by intravenous or intramuscular injections. The administration of the compound may also be made orally or per rectum. The dose for administration of the compound may be an effective amount thereof sufficient to decrease the antibody value of the auto-antibody existing in the blood stream, when being subjected later to the irradiation of the ultraviolet ray or laser light so as to excite said mono-L-aspartyl chlorin e6 or mono-L-glutamyl chlorin e6 or the salt thereof photochemically in the blood stream. The effective amount of the compound may be administered all at once or in two parts, i.e. twice, or more.

Ultraviolet ray or laser light to be irradiated may be irradiated as its beam onto the whole body or various parts of the patient, for example, the abdominal region, the leg region or the hand region over the skin thereof. Thus, the irradiation of the light may be effected in a manner that the light can transmit through the skin layer and the blood vessel wall layer so that the ultraviolet ray or laser light can reach the blood stream in the blood vessel under the skin. The irradiation may also be effected to such blood stream which is circulated extracorporeally.

The number of the times of the irradiation of ultraviolet ray or laser light may be one or more, independently upon the number of the times of the administration of the compound used. In other words, the combination of the number of times of administration of the compound with the number of times of irradiation of the ultraviolet ray or laser light may be of option so far as it is sufficient to decrease significantly the antibody value of the auto-antibody in the blood stream.

In practicing the method according to the second aspect of this invention, the total number of the times of administration of mono-L-aspartyl chlorin e6 or mono-L-glutamyl chlorin e6 or a salt thereof may, for example, be 1 time to 100 times, while the total number of the times of the irradiation of the ultraviolet ray or laser light may, for example, be 5 to 100 times. The number of the times required of both the administration of the compound and the irradiation of the light may easily be determined by preliminary testings made by those skilled in the art, according to the purposes of the therapy.

The ultraviolet ray or laser light to be irradiated is preferably such one having a wave length in a range of 620~760 nm and may be irradiated at a radiation intensity in a range of 10~100 mW/cm$^2$.

The pharmaceutical composition according to the first aspect of this invention and the photochemo-therapeutical method according to the second aspect of this invention are effective for the therapeutic treatment or prevention of a systemic auto-immune disease such as systemic lupus erythematosus, systemic pachyderma, multiple myositis, dermatomyositis or polyarteritis nodosa. This invention is expectable also for the therapy of such auto-immune diseases as auto-immune hemolytic anemia and Hashimoto's thyroiditis.

Mono-L-aspartyl or mono-L-glutamyl chlorin e6 or salt thereof as the active ingredient in the pharmaceutical composition may be administered orally or parenterally by intravenous or intramuscular injections, and others. It is also possible to administer the compound percutaneously. For instance, mono-L-aspartyl or mono-L-glutamyl chlorin e6 or salt thereof may preferably be administered after having formulated in the form of a preparation, for example, a pharmaceutical composition which is containing said compound in the form of a tetra-sodium salt and which has been lyophilized and sterilized and containing no pyrogenic substance.

For using the pharmaceutical composition according to the first aspect of this invention for oral administration, the active ingredient, mono-L-aspartyl or mono-L-glutamyl chlorin e6 or salt thereof may be admixed with a conventional solid or liquid carrier or carriers which is or are pharmacologically acceptable, and the resultant admixture may be formulated, for example, in the form of tablets, intra-oral preparations, troches, capsules, suspension, syrup, and the like.

The content of the compound as the active ingredient in the pharmaceutical composition according to the first aspect of this invention may vary depending upon the form of the preparation intended and may conveniently be in the range of about 2~60% based on the weight of the dosage unit of the preparation.

When formulating the composition according to the first aspect of this invention in the form of an injectable preparation, a preferred form of the injectable preparations is a sterile aqueous solution or dispersion or a sterile lyophilized preparation. As a preferred liquid carrier to be used here, there may be mentioned, for example, water, ethanol, glycerol, propylene glycol, vegetable oils, and the like.

Where the composition according to the first aspect of this invention is to be formulated in the form of a liquid dispersion, the dispersion state of the compound as active ingredient may be maintained well by making the active ingredient compound to have a desired particle size and by incorporating therein a viscosity regulator such as lecithin. In most cases, the liquid dispersion may preferably contain further an isotonic agent, for example, sugar or sodium chloride.

Where the composition according to the first aspect of this invention is to be formulated in the form of an injection preparation, it is possible to incorporate additionally therein an agent for delaying the absorption of the active ingredient compound, for example, aluminium mono-stearate or gelatin.

The dosage of mono-L-aspartyl or mono-L-glutamyl chlorin e6 or salt thereof to be used in this invention may vary depending upon the nature of the diseases to be treated, the purpose of the therapeutic treatment and the level of symptom, and generally it may be 0.2~10 mg per day for adult patients, while the dosage may usually be administered all at once or in several times. Optimum dosage may be determined by a suitable preliminary testing made by those skilled in the art.

As an irradiation sources for the laser light to be used for the therapy after the administration of the photosensitive compound according to this invention, there may be utilized a powerful continuous laser beam source equipped with optical filters, excited pigments, and other laser beam-feeding systems. Among the available irradiation sources of laser light as above-mentioned, it is desirable to use such a laser source which can generate a laser beam at a full output power of at least 500 mW, at a radiation intensity of 10~100 mW/cm$^2$ and at a wave-length of 620~760 nm. At present, some of commercially available laser generators can satisfy the above-mentioned requisites for the laser generation.

The acute toxicity of NPe6 which is used as one example of the photosensitive compounds to be administered in this invention, is 164 mg/kg as $LD_{50}$ value when tested on CD-1 mice (male). Further, in a photo-toxicity test with NPe6, it is found that this compound shows no reactions such as erythema, edema, etc. and is therefore a highly safe compound.

This invention is now further illustrated in more detail with reference to Test Examples and Examples, to which this invention is not limited.

TEST EXAMPLE 1

MRL/1 pr mice, which are known as a model of a spontaneous systemic auto-immune diseases, have such inherent property that they spontaneously develop the systemic auto-immune disease due to 1pr-gene. In this case, the characteristic observations of the resulting auto-immune disease include the formation of lymphoma and splenoma as caused by proliferation of heterolymphoid cells, the production of anti-ds-DNA antibody as the auto-antibody, and (or) the outbreak of lupus nephritis owing to the deposition of immune complexes, whereby an early death of the MRL/1pr mice can naturally be involved. For instance, untreated MRL/1pr mice usually have such nature that their mortality reaches 50% at 25 week-old.

To MRL/1pr mice (eight mice per group) of 18 week-old age which have been affected completely by auto-immune diseases, a solution of mono-L-aspartyl chlorin e6 tetra-sodium salt (abbreviation: NPe6) dissolved in a physiological saline solution at a NPe6 concentration of 0.1 mg/ml was intra-venously administered in such an amount to give a dosage of NPe6 of 0.5 mg/kg. After 30 minutes from the administration of NPe6, the mice were irradiated with a laser light at wave-length of 664 nm in such a manner that the skin surface on the abdominal region already shaved off of said mice would receive the laser light over a wide area of about 25 cm$^2$ per mouse tested at an intensity of 20 Joules/cm$^2$. Thus, the NPe6 contained in the blood stream within the blood vessel beneath the skin of the abdominal region of the mice was irradiated with the laser light and thereby was excited photochemically. Such photochemotherapeutic procedure comprising the intravenous administration of NPe6 and the irradiation of the laser light was applied eight times to each of the mice under test for 10 days. After 24 hours from the completion of the therapeutic treatments, which was counted from the final run of irradiation of the laser light applied to the mice of the treated group, and thus at the time when the mice tested became 19 week-old, the judgment was made about the therapeutical effects appeared on the treated mice. Further, the survival effect on the treated mice was also observed over the period of from the start of practicing this therapeutic treatments to the point of the 49 week-old age of the mice.

For the untreated group of MRL/1pr mice (10 mice per group, 18-weeks old), merely a physiological saline solution (containing no NPe6) was administered intravenously in the same amount as that for the treated group of mice, and then the mice were irradiated with a laser light as similar as the treated group of mice.

Further, examinations of the following items (1)~(4) were carried out on both the mice of the treated group and of the untreated group.

(1) An amount of the blood was taken up from the mice of 19-weeks old at the end of 24 hours after the eighth irradiation of laser light. The blood sample so taken was tested for assaying the antibody value of anti-ds-DNA antibody which is the auto-antibody in the blood, in comparison with that of the untreated group. The assay of the anti-ds-DNA antibody was done using Anti-DNA kit (Nippon Kodak Dialogenostics Co.). The level of anti-ds-DNA antibody so assayed was shown to correspond to an antibody value of 67.8±23.8 IU/ml in the untreated group but was shown to correspond to an antibody value of 5.7±5.3 IU/ml in the treated group. It was thus found that the antibody value for the anti-ds-DNA antibody was significantly and remarkably decreased by the above-mentioned photochemotherapeutic procedure.

In view of such known fact that the occurrence of the anti-ds-DNA antibody indicates a disease-specificity characteristic for systemic lupus erythematosus and can reflect the development of the disease, the above noted fact that the antibody value of the anti-ds-DNA antibody could be decreased significantly by the above-mentioned photochemo-therapeutic procedure shall suggest that the symptom of systemic lupus erythematosus could be mitigated, that is, the erythematosus could be treated with a success.

(2) An amount of the blood and an amount of urine were collected from the 19-week-old mice after the lapse of 24 hours from the 8th irradiation of the laser light. The blood samples so taken were used to determine the content of urea nitrogen in blood and the content of protein in urine, which each are indications for the functions of kidney. The content of urea nitrogen in blood and the content of protein in urine are 36.4±5.3 mg/dl and 246.2±24.0 mg/dl, respectively, for the untreated group, but are 22.3±1.4 mg/dl and 85.2±5.0 mg/dl, respectively for the treated group. Both of the content of urea nitrogen in blood and the content of protein in urine for the treated group had been decreased, as compared with those for the untreated group. This shows that the photochemo-therapeutic procedure carried out in this Example could improve the functions of kidney which had been lowered in the MRL/1pr mice.

(3) After the completion of the treatment as effected by the above-mentioned photochemotherapeutic procedure, the mice under the test were bred to be 49-weeks old and the survival rate (%) of the mice was measured once a week. The results obtained are summarily shown in Table 1 below.

TABLE 1

Survival rate (%) of the mice
(the numerals in parentheses denotes the number of surviving mice)

| Age (in weeks) of mice | Untreated group | Treated group |
|---|---|---|
| 18 | 100 (10) | 100 (8) |
| 20 | 90 (9) | 100 (8) |
| 21 | 80 (8) | 100 (8) |
| 23 | 70 (7) | 100 (8) |
| 25 | 50 (5) | 100 (8) |
| 27 | 30 (3) | 100 (8) |
| 30 | 20 (2) | 100 (8) |
| 33 | 10 (1) | 88 (7) |
| 36 | 0 (0) | 88 (7) |
| 43 | 0 (0) | 75 (6) |
| 46 | 0 (0) | 63 (5) |
| 49 | 0 (0) | 63 (5) |

The relation between the age of old (in weeks) of mice and the changes in the survival rate (%) of the mice given in Table 1 above is depicted as a graph of survival curve in FIG. 1 of the attached drawing. For instance, it is observed that in the untreated group, the survival rate (%) of the mice is only 50% at the end of 25-weeks old, but in the treated group the survival rate (%) of the surviving mice is 100% at the end of 25-weeks old and is 50% at the end of different periods of longer than the age of 49 weeks old. From this, it could be confirmed that the photochemo-therapeutically treating method according to this invention has an effect which can prolong the life-span of such mice having the nature that the mice would be spontaneously affected with a systemic auto-immune disease.

(4) An amount of blood was taken up from the 19-weeks-old mice after 24 hours from the 8th irradiation of the laser light. The content of GPT enzyme in the blood was measured for the blood sample so taken and was compared with that of the untreated group, indicating the result that no difference was found therebetween. Further, even after the eight times-repetition of the percutaneous irradiation of the laser light as above, there was not observed visually that any action of changing the skin was involved. This can suggest that there occurrs no trouble against the function of liver and also the skin by the therapeutical method of this invention.

According to a further aspect of this invention, there is provided use of mono-L-aspartyl chlorin e6 or mono-L-glutamyl chlorin e6 or a pharmacologically acceptable salt thereof, in the preparation of a pharmaceutical composition for treating an auto-immune disease photochemotherapeutically.

Further, according to further another aspect of this invention, there is provided a process for the preparation of a pharmaceutical composition for treating an auto-immune disease photochemotherapeutically, which comprises admixing mono-L-aspartyl chlorin e6 or mono-L-glutamyl chlorin e6 or a pharmacologically acceptable salt thereof with a pharmaceutically acceptable carrier or carriers.

BRIEF DESCRIPTION OF DRAWINGS

FIG. 1 is a graph showing the survival curve of the treated group of MRL/1pr mice which were subjected to the photochemo-therapeutical treatment according to this invention by administration of NPe6 and subsequent irradiation of a laser light, as well as the survival curve of the untreated group of MRL/1pr mice.

BEST MODE FOR CARRYING OUT THE INVENTION

The following Examples illustrate some examples of formulations of the pharmaceutical composition for use in the therapeutic treatment of auto-immune diseases according to the first aspect of this invention.

EXAMPLE 1

The following ingredients were admixed with each other in the following proportions by weight to prepare a base powder.

| | |
|---|---|
| Sucrose | 80.3 g |
| Tapioca starch | 13.2 g |
| Magnesium stearate | 4.4 g |

The base powder so prepared was mixed with an appropriate amount of NPe6, and the mixture was pressed into tablets in a conventional manner to give tablets each containing 100 mg of NPe6 as active ingredient.

EXAMPLE 2

NPe6 (200 mg) was dissolved in a physiological saline solution to give a final concentration of NPe6 of 20 mg/ml.

The resulting solution was subjected to a sterilizing treatment to prepare an injectable composition which was suitable for intravenous and intramuscular administrations.

INDUSTRIAL APPLICABILITY

As explained above, this invention is to carry out a method comprising administration of mono-L-aspartyl chlorin e6 or mono-L-glutamyl chlorin e6 or a pharmacologically acceptable salt thereof to a patient having an auto-immune diseases, followed by irradiation of the blood stream containing said compound with an ultraviolet ray or a laser light and thereby is able to decrease significantly the level of the auto-antibody in the blood of the patient. Therefore, this invention is effective to treat photochemotherapeutically a variety of auto-immune diseases, such as systemic lupus erythematosus, systemic pachyderma, multiple myositis, dermatomyotisis and polyarteritis nodosa, and others.

What is claimed is:

1. A method for photochemotherapeutically treating systemic lupus erythematosus in a patient in need thereof, which comprises:
   a) administering orally or parenterally to a patient being treated for systemic lupus erythematosus a compound selected from the group consisting of mono-L-aspartyl chlorin e6, mono-L-glutamyl chlorin e6, or pharmacologically acceptable salts thereof, at a dosage of about 0.2 to about 10 mg per day:
   b) irradiating percutaneously the blood stream containing the administered compound within the blood vessels of the entire body, or a part or parts of the body of the patient, or irradiating an extracorporeally circulated blood stream containing the administered compound, with a laser light of a wavelength of about 620 to about 760 nm at a radiation intensity of about 10 to about 100 mW/cm$^2$, thereby subjecting said compound to exposure with the irradiating laser light whereby said compound is excited photochemically.

2. The method of claim 1 wherein the percutaneous irradiation is repeated between one and one hundred times.

3. A method for photochemotherapeutically treating systemic pachyderma in a patient in need thereof, which comprises:
   a) administering orally or parenterally to a patient being treated for systemic pachyderma a compound selected from the group consisting of mono-L-aspartyl chlorin e6, mono-L-glutamyl chlorin e6, or pharmacologically acceptable salts thereof, at a dosage of about 0.2 to about 10 mg per day:
   b) irradiating percutaneously the blood stream containing the administered compound within the blood vessels of the entire body, or a part or parts of the body of the patient, or irradiating an extracorporeally circulated blood stream containing the administered compound, with a laser light of a wavelength of about 620 to about 760 nm at a radiation intensity of about 10 to about 100 mW/cm$^2$, thereby subjecting said compound to exposure with the irradiating laser light whereby said compound is excited photochemically.

4. The method of claim 3 wherein the percutaneous irradiation is repeated between one and one hundred times.

* * * * *